(12) United States Patent
Thomas

(10) Patent No.: US 6,906,065 B2
(45) Date of Patent: Jun. 14, 2005

(54) 4-AMINO-5-CYANO-2-ANILINO-PYRIMIDINE DERIVATIVES AND THEIR USE AS INHIBITORS OF CELL-CYCLE KINASES

(75) Inventor: Andrew Peter Thomas, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 20 days.

(21) Appl. No.: 10/239,790

(22) PCT Filed: Mar. 23, 2001

(86) PCT No.: PCT/GB01/01264

§ 371 (c)(1), (2), (4) Date: Sep. 25, 2002

(87) PCT Pub. No.: WO01/72717

PCT Pub. Date: Oct. 4, 2001

(65) Prior Publication Data

US 2003/0087923 A1 May 8, 2003

(30) Foreign Application Priority Data

Mar. 28, 2000 (GB) .............................. 0007371

(51) Int. Cl.⁷ ..................... C07D 239/48; A61K 31/505
(52) U.S. Cl. .................... 514/235.8; 514/275; 544/122; 544/323; 544/324
(58) Field of Search ................................. 544/122, 323, 544/324; 514/235.8, 275

(56) References Cited

U.S. PATENT DOCUMENTS

| | | | |
|---|---|---|---|
| 4,983,608 A | 1/1991 | Effland et al. | 514/216 |
| 5,516,775 A | 5/1996 | Zimmermann et al. | 514/224.2 |
| 5,521,184 A | 5/1996 | Zimmermann | 514/252 |
| 5,610,303 A | 3/1997 | Kimura et al. | 544/326 |
| 5,739,143 A | 4/1998 | Adams et al. | 514/275 |
| 5,859,041 A | 1/1999 | Liverton et al. | 514/396 |
| 5,985,877 A | 11/1999 | Dionne et al. | 514/250 |

FOREIGN PATENT DOCUMENTS

| | | |
|---|---|---|
| CA | 2231765 | 9/1998 |
| EP | 0 135 472 | 3/1985 |
| EP | 0 363 002 | 4/1990 |
| EP | 0 379 806 B1 | 8/1990 |
| EP | 0 564 409 B1 | 10/1993 |
| EP | 0 945 443 A1 | 9/1999 |
| WO | 91/18887 | 12/1991 |
| WO | 92/20642 | 11/1992 |
| WO | 95/09847 | 4/1995 |
| WO | 95/09851 | 4/1995 |
| WO | 95/09852 | 4/1995 |
| WO | 95/09853 | 4/1995 |
| WO | 95/15952 | 6/1995 |
| WO | 96/05177 | 2/1996 |
| WO | 96/28427 | 9/1996 |
| WO | 96/33980 | 10/1996 |
| WO | 96/40143 | 12/1996 |
| WO | 97/19065 | 5/1997 |
| WO | 97/35856 | 10/1997 |
| WO | 97/40017 | 10/1997 |
| WO | 97/44326 | 11/1997 |
| WO | 97/47618 | 12/1997 |
| WO | 98/11095 | 3/1998 |
| WO | 98/16230 | 4/1998 |
| WO | 98/18782 | 5/1998 |
| WO | 98/25619 | 6/1998 |
| WO | 98/33798 A | 8/1998 |
| WO | 98/41512 | 9/1998 |
| WO | 98/54093 | 12/1998 |
| WO | 98/56788 | 12/1998 |
| WO | 99/01136 | 1/1999 |
| WO | 99/32121 | 1/1999 |
| WO | 99/18096 | 4/1999 |
| WO | 99/18942 | 4/1999 |
| WO | 99/31073 | 6/1999 |
| WO | 99/41253 | 8/1999 |
| WO | 99/50250 | 10/1999 |
| WO | 99/50251 | 10/1999 |

(Continued)

OTHER PUBLICATIONS

Traxler, Protein tyrosine kinase inhibitors in cancer treatment, Exp. Opin. Ther. Patents, 7(6): 571–588, 1997.*

Bennett, Cecil Textbook of Medicine, 20th Ed., vol. 1, 1997, pp. 1004–1010.

(Continued)

*Primary Examiner*—Deepak Rao
(74) *Attorney, Agent, or Firm*—Morgan, Lewis & Bockius LLP

(57) ABSTRACT

Compounds of formula (I) wherein: $R^1$ is halo, nitro, cyano, hydroxy, amino, carboxy, carbamoyl, mercapto, $C_{1-6}$alkyl, $C_{2-6}$alkenyl or $C_{2-6}$alkynyl; p is 0–4; wherein the values of $R^1$ may be the same or different; $R^2$ is sulphamoyl or a group B-E- ; wherein B is optionally substituted as defined within and is selected from $C_{1-6}$alkyl, $C_{2-6}$alkenyl, $C_{2-6}$alkynyl, $C_{3-8}$cycloalkyl, $C_{1-6}$alkyl, phenyl, a heterocyclic group, phenyl$C_{1-6}$alkyl or (heterocyclic group)$C_{1-6}$alkyl; E is $C(O)-$, $N(R^a)C(O)-$, $-C(O)N(R^a)-$, $-S(O)_r-$, $-SO_2N(R^a)-$ or $-N(R^a)SO_2-$; wherein $R^a$ is hydrogen or $C_{1-6}$alkyl optionally substituted as defined within and r is 1–2; q is 0–2; wherein the values of $R^2$ may be the same or different; and wherein p+q=1–5; or a pharmaceutically acceptable salt or an in vivo hydrolysable ester thereof are described. Processes for their manufacture and their use as inhibitors of cell cycle kinases, particularly CDK2, CDK4 and/or CDK6 are also described (I)

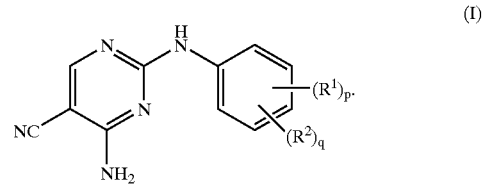

11 Claims, No Drawings

FOREIGN PATENT DOCUMENTS

| | | |
|---|---|---|
| WO | 00/12485 | 3/2000 |
| WO | 00/12486 | 3/2000 |
| WO | 00/17202 | 3/2000 |
| WO | 00/17203 | 3/2000 |
| WO | 00/21926 | 4/2000 |
| WO | 00/25780 | 5/2000 |
| WO | 00/26209 | 5/2000 |
| WO | 00/39101 A | 7/2000 |
| WO | 00/44750 | 8/2000 |
| WO | 00/49018 | 8/2000 |
| WO | 00/53595 | 9/2000 |
| WO | 00/55161 | 9/2000 |
| WO | 00/59892 | 10/2000 |
| WO | 00/78731 A1 | 12/2000 |
| WO | 01/14375 A1 | 3/2001 |
| WO | 01/29009 A1 | 4/2001 |
| WO | 01/30778 A1 | 5/2001 |
| WO | 01/37835 A1 | 5/2001 |
| WO | 01/47897 A1 | 7/2001 |
| WO | 01/47921 A1 | 7/2001 |
| WO | 01/60816 A1 | 8/2001 |
| WO | 01/64653 A1 | 9/2001 |
| WO | 01/64654 A1 | 9/2001 |
| WO | 01/64655 A1 | 9/2001 |
| WO | 01/64656 A1 | 9/2001 |
| WO | 02/04429 A1 | 1/2002 |
| WO | 02/20512 A1 | 3/2002 |
| WO | 02/066481 A1 | 8/2002 |
| WO | 02/096887 A1 | 12/2002 |

OTHER PUBLICATIONS

Boschelli et al., Synthesis and Tyrosine Kinase Inhibitory Activity of a Series of 2–Amino–8–H–pyrido[2,3–d]pyrimidines: Identifidation of Potent, Selective Platelet–Derived Growth Factor Receptor Tyrosine Kinase Inhibitors, J. Med. Chem., vol. 41, 1998, pp. 4365–4377.

Donnellan et al., "Cyclin E in human cancers", FASEB Journal, 13, 1999, pp. 773–780.

Ghosh, "2,4–Bis(Arylamino)–6–Methyl Pyrimidines as Antimicrobial Agents", J. Indian Chem. Soc., vol. 58, No. 5, 1981, pp. 512–513

El–Kerdawy et al.; "2,4–Bis (Substituted)–5–Nitropyrimidines of Expected Diuretic Action"; Egypt J. Chem. vol. 29, No. 2, 1986, pp. 247–251.

Fiziol Akt Veshchestva, 1975, vol. 7, pp. 68–72.

Ghosh et al.; "2,4–Bis(arylamino)–5–methylpyrimidines as Antimicrobial Agents"; J. Med. Chem., 1967, vol. 10, No. 5, pp. 974–975.

Ghosh, "2,4–Bis(arylamino)–6–methylpyrimidines as an antimicrobial agents", Chemical Abstract No. 97712f, vol. 95, 1981, pp. 648.

Kornberg, "Focal adhesion kinase and its potential involvement in tumor invasion and metastasis", Head Neck 20(8): 1998, pp. 745–752.

Griffiths et al., "Androgens, Androgen Receptors, Antiandrogens and the Treatment of Prostate Cancer", European Urology, vol. 32, No. Suppl. 3, 1997, pp. 24–40, XP001013446.

Woodburn et al., "ZD1839, an epidermal growth factor tyrosine kinase inhibitor selected for clinical development", Proceedings of the Annual Meeting of the American Association for Cancer Research, vol. 38, 1997, p. 633 XP001009911, Abstract.

Deady et al., "Reactions of some quinazoline compounds with ethoxymethyulenemalonic acid derivatives", J. Heterocycl. Chem., vol. 26, No. 1, 1989, pp. 161–168 XP001000831, examples 14, 16B.

Zimmerman et al., "Phenylamino–Pyrimidine (PAP) Derivatives: A New Class of Potent and Selective Inhibitors of Protein Kinase C (PKC)", Archiv. der Pharmazie, DE, VCH Verlagsgesellschaft MBH, Weinheim, vol. 329, No. 7, Jul. 1996, pp. 371–376, XP000885618, ISSN: 0365–6233, examples 5–36.

Schmidt et al., "A convenient synthesis of 2–substituted 4–amino–5–pyrimidinecarbonitriles", J. Heterocycl. Chem., vol. 24, No. 5, 1987, pp. 1305–1307, XP001000522, p. 2, Example 7E.

* cited by examiner

4-AMINO-5-CYANO-2-ANILINO-PYRIMIDINE DERIVATIVES AND THEIR USE AS INHIBITORS OF CELL-CYCLE KINASES

The invention relates to pyrimidine derivatives, or pharmaceutically acceptable salts or in vivo hydrolysable esters thereof, which possess cell-cycle inhibitory activity and are accordingly useful for their anti-cell-proliferation (such as anti-cancer) activity and are therefore useful in methods of treatment of the human or animal body. The invention also relates to processes for the manufacture of said pyrimidine derivatives, to pharmaceutical compositions containing them and to their use in the manufacture of medicaments of use in the production of an anti-cell-proliferation effect in a warm-blooded animal such as man.

A family of intracellular proteins called cyclins play a central role in the cell cycle. The synthesis and degradation of cyclins is tightly controlled such that their level of expression fluctuates during the cell cycle. Cyclins bind to cyclin-dependent serine/threonine kinases (CDKs) and this association is essential for CDK (such as CDK1, CDK2, CDK4 and/or CDK6) activity within the cell. Although the precise details of how each of these factors combine to regulate CDK activity is poorly understood, the balance between the two dictates whether or not the cell will progress through the cell cycle.

The recent convergence of oncogene and tumour suppressor gene research has identified regulation of entry into the cell cycle as a key control point of mitogenesis in tumours. Moreover, CDKs appear to be downstream of a number of oncogene signalling pathways. Disregulation of CDK activity by upregulation of cyclins and/or deletion of endogenous inhibitors appears to be an important axis between mitogenic signalling pathways and proliferation of tumour cells.

Accordingly it has been recognised that an inhibitor of cell cycle kinases, particularly inhibitors of CDK2, CDK4 and/or CDK6 (which operate at the S-phase, G1-S and G1-S phase respectively) should be of value as a selective inhibitor of cell proliferation, such as growth of mammalian cancer cells.

The present invention is based on the discovery that certain pyrimidine compounds surprisingly inhibit the effects of cell cycle kinases showing selectivity for CDK2, CDK4 and CDK6, and thus possess anti-cell-proliferation properties. Such properties are expected to be of value in the treatment of disease states associated with aberrant cell cycles and cell proliferation such as cancers (solid tumours and leukemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Accordingly, the present invention provides a compound of formula (I):

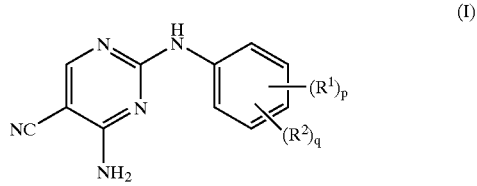

(I)

wherein:

$R^1$ is halo, nitro, cyano, hydroxy, amino, carboxy, carbamoyl, mercapto, $C_{1-6}$alkyl, $C_{2-6}$alkenyl or $C_{2-6}$alkynyl;

p is 0–4; wherein the values of $R^1$ may be the same or different;

$R^2$ is sulphamoyl or a group B-E-; wherein

B is selected from $C_{1-6}$alkyl, $C_{2-6}$alkenyl, $C_{2-6}$alkynyl, $C_{3-8}$cycloalkyl, $C_{3-8}$cycloalkylC$_{1-6}$alkyl, phenyl, a heterocyclic group, phenylC$_{1-6}$alkyl or (heterocyclic group)C$_{1-6}$alkyl; wherein said $C_{1-6}$alkyl, $C_{2-6}$alkenyl, $C_{2-6}$alkynyl, $C_{3-8}$cycloalkyl, $C_{3-8}$cycloalkylC$_{1-6}$alkyl, phenyl, heterocyclic group, phenylC$_{1-6}$alkyl or (heterocyclic group)C$_{1-6}$alkyl are optionally substituted on carbon by one or more D; and wherein if said heterocyclic group contains an —NH— moiety that nitrogen may be optionally substituted by a group selected from G;

E is —C(O)—, —N(R$^a$)C(O)—, —C(O)N(R$^a$)—, —S(O)$_r$—, —SO$_2$N(R$^a$)— or —N(R$^a$)SO$_2$—; wherein R$^a$ is hydrogen or $C_{1-6}$alkyl optionally substituted by one or more D and r is 1–2;

D is independently selected from halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl and N,N-($C_{1-6}$alkyl)$_2$sulphamoyl;

G is selected from $C_{1-4}$alkyl, $C_{1-4}$alkanoyl, $C_{1-4}$alkylsulphonyl, $C_{1-4}$alkoxycarbonyl, carbamoyl, N-($C_{1-4}$alkyl)carbamoyl, N,N-($C_{1-4}$alkyl)carbamoyl, benzyl, benzyloxycarbonyl, benzoyl and phenylsulphonyl; and q is 0–2; wherein the values of $R^2$ maybe the same or different; and wherein p+q=1–5;

or a pharmaceutically acceptable salt or an in vivo hydrolysable ester thereof

In another aspect of the invention, there is provided a compound of formula (I) or a pharmaceutically acceptable salt or an in vivo hydrolysable ester thereof with the proviso that that compound is not 2-(2,4-dimethylanilino)-4-amino-5-cyanopyrimidine.

In this specification the term "alkyl" includes both straight and branched chain alkyl groups but references to individual alkyl groups such as "propyl" are specific for the straight chain version only. For example, "$C_{1-6}$alkyl" includes $C_{1-4}$alkyl, $C_{1-3}$alkyl, propyl, isopropyl and t-butyl. However, references to individual alkyl groups such as 'propyl' are specific for the straight chained version only and references to individual branched chain alkyl groups such as 'isopropyl' are specific for the branched chain version only. A similar convention applies to other radicals, for example "phenylC$_{1-6}$alkyl" includes phenylC$_{1-4}$alkyl, benzyl, 1-phenylethyl and 2-phenylethyl. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

A "heterocyclic group" is a saturated, partially saturated or unsaturated, mono or bicyclic ring containing 4–12 atoms of which at least one atom is chosen from nitrogen, sulphur or oxygen, which may, unless otherwise specified, be carbon or nitrogen linkled, wherein a —CH$_2$— group can optionally be replaced by a —C(O)—, a ring nitrogen atom may optionally bear a $C_{1-6}$alkyl group and form a quaternary compound or a ring nitrogen and/or sulphur atom may be optionally oxidised to form the N-oxide and or the S-oxides. Examples and suitable values of the term "heterocyclic group" are morpholino, piperidyl, pyridyl, pyranyl, pyrrolyl, isothiazolyl, indolyl, quinolyl, thienyl, 1,3-benzodioxolyl, thiadiazolyl, piperazinyl, thiazolidinyl, pyrrolidinyl, thiomorpholino, pyrrolinyl, homopiperazinyl, 3,5-dioxapiperidinyl, tetrahydropyranyl, imidazolyl, pyrimidyl, pyrazinyl, pyridazinyl, isoxazolyl, N-methylpyrrolyl, 4-pyridone, 1-isoquinolone, 2-pyrrolidone, 4-thiazolidone, pyridine-N-oxide and quinoline-N-oxide. Preferably a "heterocyclic group" is a saturated, partially saturated or unsaturated, mono or bicyclic ring containing 5 or 6 atoms of which at least one atom is chosen from nitrogen, sulphur or oxygen, it may, unless otherwise specified, be carbon or nitrogen linked, a —$CH_2$— group can optionally be replaced by a —C(O)— and a ring sulphur atom may be optionally oxidised to form the S-oxides. More preferably a "heterocyclic group" is tetrahydrofuryl, pyridyl, pyrrolidinonyl, morpholino, imidazolyl, piperidinyl or pyrrolidinyl.

An example of "$C_{1-6}$alkanoyloxy" is acetoxy. Examples of "$C_{1-6}$alkoxycarbonyl" include $C_{1-4}$alkoxycarbonyl, methoxycarbonyl, ethoxycarbonyl, n- and t-butoxycarbonyl. Examples of "$C_{1-6}$alkoxy" include methoxy, ethoxy and propoxy. Examples of "$C_{1-6}$alkanoylamino" include formamido, acetamido and propionylamino. Examples of "$C_{1-6}$alkylS(O)$_a$ wherein a is 0 to 2" include $C_{1-4}$alkylsulphonyl, methylthio, ethylthio, methylsulphinyl, ethylsulphinyl, mesyl and ethylsulphonyl. Examples of "$C_{1-6}$alkylS(O)$_r$ wherein r is 1 to 2" include methylsulphinyl, ethylsulphinyl, mesyl and ethylsulphonyl. Examples of "$C_{1-6}$alkanoyl" include $C_{1-4}$alkanoyl, propionyl and acetyl. Examples of "N-$C_{1-6}$alkylamino" include methylamino and ethylamino. Examples of "N,N-($C_{1-6}$alkyl)$_2$amino" include di-N-methylamino, di-(N-ethyl)amino and N-ethyl-N-methylamino. Examples of "$C_{2-6}$alkenyl" are vinyl, allyl and 1-propenyl Examples of "$C_{2-6}$alkynyl" are ethynyl, 1-propynyl and 2-propynyl. Examples of "N-($C_{1-6}$alkyl)sulphamoyl" are N-(methyl)sulphamoyl and N-(ethyl)sulphamoyl. Examples of "N-($C_{1-6}$alkyl)$_2$sulphamoyl" are N,N-(dimethyl)sulphamoyl and N-(methyl)-N-(ethyl)sulphamoyl. Examples of "N-($C_{1-6}$alkyl)carbamoyl" are N-($C_{1-4}$alkyl)carbamoyl, methylaminocarbonyl and ethylaminocarbonyl. Examples of "N,N-($C_{1-6}$alkyl)$_2$carbamoyl" are N,N-($C_{1-4}$alkyl)$_2$carbamoyl, dimethylaminocarbonyl and methylethylaminocarbonyl. Examples of "$C_{3-8}$cycloalkyl" are cyclopropyl, cyclobutyl, cyclopropyl and cyclohexyl. Examples of "(heterocyclic group)$C_{1-6}$alkyl" include pyridylmethyl, 3-morpholinopropyl and 2-pyrimid-2-ylethyl. Examples of "$C_{3-8}$cycloalkyl$C_{1-6}$alkyl" are cyclopropylethyl, cyclobutylmethyl, 2-cyclopropylpropyl and cyclohexylethyl.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

The compounds of the formula (I) may be administered in the form of a pro-drug which is broken down in the human or animal body to give a compound of the formula (I). Examples of pro-drugs include in vivo hydrolysable esters of a compound of the formula (I).

An in vivo hydrolysable ester of a compound of the formula (I) containing carboxy or hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

Some compounds of the formula (I) may have chiral centres and/or geometric isomeric centres (E- and Z-isomers), and it is to be understood that the invention encompasses all such optical, diastereoisomers and geometric isomers that possess CDK inhibitory activity.

The invention relates to any and all tautomeric forms of the compounds of the formula (I) that possess CDK inhibitory activity.

It is also to be understood that certain compounds of the formula (I) can exist in solvated as well as unsolvated forms such as, for example, hydrated forms. It is to be understood that the invention encompasses all such solvated forms which possess CDK inhibitory activity.

Preferred values of $R^1$, $R^2$, p and q are as follows. Such values may be used where appropriate with any of the definitions, claims or embodiments defined hereinbefore or hereinafter.

Preferably $R^1$ is halo or $C_{1-2}$alkyl.
More preferably $R^1$ is fluoro, chloro or methyl.
Particularly $R^1$ is fluoro or chloro.
More particularly $R^1$ is chloro.
Preferably $R^1$ is meta or para to the amino group of the aniline in formula (I).
More preferably $R^1$ is meta to the amino group of the aniline in formula (I).
Preferably p is 0–2; wherein the values of $R^1$ may be the same or different.
More preferably p is 0 or 1.
In one aspect of the invention preferably p is 0.
In another aspect of the invention preferably p is 1.
In a further aspect of the invention preferably p is 2; wherein the values of $R^1$ may be the same or different.
Preferably $R^2$ is sulphamoyl or a group B-E-; wherein
B is selected from $C_{1-6}$alkyl, $C_{2-6}$alkenyl, $C_{3-8}$cycloalkyl, $C_{3-8}$cycloalkyl$C_{1-6}$alkyl, phenyl$C_{1-6}$alkyl or (heterocyclic group)$C_{1-6}$alkyl; wherein said $C_{1-6}$alkyl, $C_{2-6}$alkenyl, $C_{3-8}$cycloalkyl, $C_{3-8}$cycloalkyl$C_{1-6}$alkyl, phenyl$C_{1-6}$alkyl or (heterocyclic group)$C_{1-6}$alkyl are optionally substituted on carbon by one or more D; and wherein if said heterocyclic group contains an —NH— moiety that nitrogen may be optionally substituted by a group selected from G;

E is —N($R^a$)$SO_2$—; wherein $R^a$ is hydrogen;

D is independently selected from halo, hydroxy, $C_{1-6}$alkoxy or N-($C_{1-6}$alkyl)amino, N,N-($C_{1-6}$alkyl)$_2$amino; and G is $C_{1-4}$alkyl.

More preferably $R^2$ is sulphamoyl or a group B-E-; wherein

B is optionally substituted by D and is selected from ethyl, propyl, pentyl, allyl, cyclopropyl, cyclobutyl, cyclopropylmethyl, benzyl, phenethyl, tetrahydrofurylmethyl, pyridylethyl, pyrrolidinonylpropyl, morpholinopropyl, imidazolylpropyl, piperidinylethyl, pyrrolidinylethyl (optionally substituted on the ring nitrogen by methyl), E is —$NHSO_2$—;

D is independently selected from fluoro, hydroxy, methoxy, ethoxy, isopropoxy, isopropylamino and dimethylamino.

Particularly $R^2$ is selected from sulphamoyl, N-(cyclopropylmethyl)sulphamoyl, N-(tetrahydrofur-2-ylmethyl)sulphamoyl, N-(2-methoxyethyl)sulphamoyl, N-(2-pyrid-2-ylethyl)sulphamoyl, N-(2-piperidin-1-ylethyl)sulphamoyl, N-[2-(1-methylpyrrolidin-2-yl)ethyl]sulphamoyl, N-(2-isopropylaminoethyl)sulphamoyl, N-(2,2,2-trifluoroethyl)sulphamoyl, N-(3-methoxypropyl)sulphamoyl, N-(3-ethoxypropyl)sulphamoyl, N-(3-isopropoxypropyl)sulphamoyl, N-(3-dimethylaminopropyl)sulphamoyl, N-[3-(2-oxopyrrolidin-1-yl)propyl]sulphamoyl, N-(3-morpholinopropyl)sulphamoyl, N-(3-imidazol-1-ylpropyl)sulphamoyl, N-(3-isopropylaminopropyl)sulphamoyl, N-(propyl)sulphamoyl, N-(pentyl)sulphamoyl, N-(allyl)sulphamoyl, N-(cyclopropyl)sulphamoyl, N-(cyclobutyl)sulphamoyl, N-(3-methoxybenzyl)sulphamoyl, N-(4-fluorobenzyl)sulphamoyl, N-(phenethyl)sulphamoyl, N-(4-hydroxyphenethyl)sulphamoyl and N-(4-methoxyphenethyl)sulphamoyl.

In another aspect of the invention, preferably $R^2$ is sulphamoyl or a group B-E-; wherein B is selected from $C_{1-6}$alkyl, $C_{1-6}$alkenyl, $C_{3-8}$cycloalkyl, $C_{3-8}$cycloalkyl$C_{1-6}$alkyl, phenyl$C_{1-6}$alkyl or (heterocyclic group)$C_{1-6}$alkyl; wherein said $C_{1-6}$alkyl, $C_{2-6}$alkenyl, $C_{3-8}$cycloalkyl, $C_{3-8}$cycloakyl$C_{1-6}$alkyl, phenyl$C_{1-6}$alkyl or (heterocyclic group)$C_{1-6}$alkyl are optionally substituted on carbon by one or more D; and wherein if said heterocyclic group contains an —NH— moiety that nitrogen may be optionally substituted by a group selected from G;

E is —N($R^a$)$SO_2$— or —N($R^a$)C(O)—; wherein $R^a$ is hydrogen;

D is independently selected from halo, hydroxy, $C_{1-6}$alkoxy or N-($C_{1-6}$alkyl)amino, N,N-($C_{1-6}$alkyl)$_2$amino; and G is $C_{1-4}$alkyl.

In another aspect of the invention, more preferably $R^2$ is sulphamoyl or a group B-E-; wherein B is optionally substituted by D and is selected from ethyl, propyl, pentyl, 2,2-dimethylpropyl, allyl, cyclopropyl, cyclobutyl, cyclopropylmethyl, benzyl, phenethyl, tetrahydrofurylmethyl, pyridylethyl, pyrrolidinonylpropyl, morpholinopropyl, imidazolylpropyl, piperidinylethyl, pyrrolidinylethyl (optionally substituted on the ring nitrogen by methyl), E is —$NHSO_2$— or —N($R^a$)C(O)—;

D is independently selected from fluoro, hydroxy, methoxy, ethoxy, isopropoxy, isopropylamino and dimethylamino.

In another aspect of the invention, particularly $R^2$ is selected from sulphamoyl, N-(cyclopropylmethyl)sulphamoyl, N-(tetrahydrofur-2-ylmethyl)sulphamoyl, N-(2-methoxyethyl)sulphamoyl, N-(2-pyrid-2-ylethyl)sulphamoyl, N-(2-piperidin-1-ylethyl)sulphamoyl, N-[2-(1-methylpyrrolidin-2-yl)ethyl]sulphamoyl, N-(2-isopropylaminoethyl)sulphamoyl, N-(9,2,2-trifluoroethyl)sulphamoyl, N-(2-dimethylaminoethyl)sulphamoyl, N-(3-methoxypropyl)sulphamoyl, N-(3-ethoxypropyl)sulphamoyl, N-(3-isopropoxypropyl)sulphamoyl, N-(3-dimethylaminopropyl)sulphamoyl, N-[3-(2-oxopyrrolidin-1-yl)propyl]sulphamoyl, N-(3-morpholinopropyl)sulphamoyl, N-(3-imidazol-1-ylpropyl)sulphamoyl, N-(3-isopropylaminopropyl)sulphamoyl, N-(propyl)sulphamoyl, N-(3-hydroxy-2,2-dimethylpropyl)sulphamoyl, N-(pentyl)sulphamoyl, N-(allyl)sulphamoyl, N-(cyclopropyl)sulphamoyl, N-(cyclobutyl)sulphamoyl, N-(3-methoxybenzyl)sulphamoyl, N-(4-fluorobenzyl)sulphamoyl, N-(phenethyl)sulphamoyl, N-(4-hydroxyphenethyl)sulphamoyl, N-(4-methoxyphenethyl)sulphamoyl and N-(3-imidazol-1-ylpropyl)carbamoyl.

Preferably $R^2$ is meta or para to the amino group of the aniline in formula (I).

More preferably $R^2$ is para to the amino group of the aniline in formula (I).

Preferably E is —$NHSO_2$—.

In another aspect of the invention, preferably E is —$NHSO_2$— or —N($R^a$)C(O)—.

Preferably q is 0 or 1.

In one aspect of the invention preferably q is 0.

In another aspect of the invention preferably q is 1.

In a further aspect of the invention preferably q is 2; wherein the values of $R^2$ may be the same or different.

Preferably p+q=1 or 2.

More preferably p+q=1.

Therefore in one aspect of the invention, there is provided a compound of formula (I) as depicted above wherein:

$R^1$ is halo or $C_{1-2}$alkyl;

p is 0–2; wherein the values of $R^1$ may be the same or different;

$R^2$ is sulphamoyl or a group B-E-; wherein

B is selected from $C_{1-6}$alkyl, $C_{2-6}$alkenyl, $C_{3-8}$cycloalkyl, $C_{3-8}$cycloalkyl$C_{1-6}$alkyl, phenyl$C_{1-6}$alkyl or (heterocyclic group)$C_{1-6}$alkyl; wherein said $C_{1-6}$alkyl, $C_{2-6}$alkenyl, $C_{3-8}$cycloalkyl, $C_{3-8}$cycloalkyl$C_{1-6}$alkyl, phenyl$C_{1-6}$alkyl or (heterocyclic group)$C_{1-6}$alkyl are optionally substituted on carbon by one or more D; and wherein if said heterocyclic group contains an —NH— moiety that nitrogen may be optionally substituted by a group selected from G;

E is —N($R^a$)$SO_2$—; wherein $R^1$ is hydrogen;

D is independently selected from halo, hydroxy, $C_{1-6}$alkoxy or N-($C_{1-6}$alkyl)amino, N,N-($C_{1-6}$alkyl)$_2$amino;

G is $C_{1-4}$alkyl; and q is 0 or 1; and p+q=1 or 2;

or a pharmaceutically acceptable salt or an in vivo hydrolysable ester thereof.

Therefore in a further aspect of the invention, there is provided a compound of formula (I) as depicted above wherein:

$R^1$ is fluoro, chloro or methyl;

p is 0 or 1;

$R^2$ is sulphamoyl or a group B-E-; wherein

B is optionally substituted by D and is selected from ethyl, propyl, pentyl, allyl, cyclopropyl, cyclobutyl, cyclopropylmethyl, benzyl, phenethyl, tetrahydrofurylmethyl, pyridylethyl, pyrrolidinonylpropyl, morpholinopropyl, imidazolylpropyl, piperidinylethyl, pyrrolidinylethyl (optionally substituted on the ring nitrogen by methyl);

E is —NHSO$_2$—;

D is independently selected from fluoro, hydroxy, methoxy, ethoxy, isopropoxy, isopropylamino and dimethylamino; and q is 0 or 1; and p+q=1 or 2;

or a pharmaceutically acceptable salt or an in vivo hydrolysable ester thereof.

Therefore in an additional aspect of the invention, there is provided a compound of formula (I) as depicted above wherein:

p is 0;

R$^2$ is selected from sulphamoyl, N-(cyclopropylmethyl)sulphamoyl, N-(tetrahydrofur-2-ylmethyl)sulphamoyl, N-(2-methoxyethyl)sulphamoyl, N-(2-pyrid-2-ylethyl)sulphamoyl, N-(2-piperidin-1-ylethyl)sulphamoyl, N-[2-(1-methylpyrrolidin-2-yl)ethyl]sulphamoyl, N-(2-isopropylaminoethyl)sulphamoyl, N-(2,2,2-trifluoroethyl)sulphamoyl, N-(3-methoxypropyl)sulphamoyl, N-(3-ethoxypropyl)sulphamoyl, N-(3-isopropoxypropyl)sulphamoyl, N-(3-dimethylaminopropyl)sulphamoyl, N-[3-(2-oxopyrrolidin-1-yl)propyl]sulphamoyl, N-(3-morpholinopropyl)sulphamoyl, N-(3-imidazol-1-ylpropyl)sulphamoyl, N-(3-isopropylaminopropyl)sulphamoyl, N-(propyl)sulphamoyl, N-(pentyl)sulphamoyl, N-(allyl)sulphamoyl, N-(cyclopropyl)sulphamoyl, N-(cyclobutyl)sulphamoyl, N-(3-methoxybenzyl)sulphamoyl, N-(4-fluorobenzyl)sulphamoyl, N-(phenethyl)sulphamoyl, N-(4-hydroxyphenethyl)sulphamoyl and N-(4-methoxyphenethyl)sulphamoyl; and q is 1;

or a pharmaceutically acceptable salt or an in vivo hydrolysable ester thereof.

In another aspect of the invention, preferred compounds of the invention are any one of Examples 1–27 or a pharmaceutically acceptable salt or an in vivo hydrolysable esters thereof.

In another aspect of the invention, preferred compounds of the invention are any one of Examples 1–31 or a pharmaceutically acceptable salt or an in vivo hydrolysable esters thereof.

In a further aspect of the invention, preferred compounds of formula (I) are:
4-amino-5-cyano-2-{4-[N-(2-methoxyethyl)sulphamoyl]anilino}pyrimidine;
4-amino-5-cyano-2-{4-[N-(tetrahydrofur-2-ylmethyl)sulphamoyl]anilino}pyrimidine;
4-amino-5-cyano-2-{4-[N-(4-fluorobenzyl)sulphamoyl]anilino}pyrimidine;
4-amino-5-cyano-2-{4-[N-(3-methoxypropyl)sulphamoyl]anilino}pyrimidine;
4-amino-5-cyano-2-{4-[N-(cyclopropyl)sulphamoyl]anilino}pyrimidine;
4-amino-5-cyano-2-[4-(N-allylsulphamoyl)anilino]pyrimidine;
4-amino-5-cyano-2-[4-(N-propylsulphamoyl)anilino]pyrimidine;
4-amino-5-cyano-2-{4-[N-(2-isopropylaminoethyl)sulphamoyl]anilino}pyrimidine;
4-amino-5-cyano-2-{4-[N-(3-isopropylaminopropyl)sulphamoyl]anilino}pyrimidine; and
4-amino-5-cyano-2-{4-[N-(2-piperidinoethyl)sulphamoyl]anilino}pyrimidine;

or a pharmaceutically acceptable salt or an in vivo hydrolysable ester thereof.

Preferred aspects of the invention are those which relate to the compound of formula (I) or a pharmaceutically acceptable salt thereof.

Another aspect of the present invention provides a process for preparing a compound of formula (I) or a pharmaceutically acceptable salt or an in vivo hydrolysable ester thereof which process (wherein R$^1$, R$^2$, p and q are, unless otherwise specified, as defined in formula (I)) comprises of:

a) reaction of a pyrimidine of formula (II):

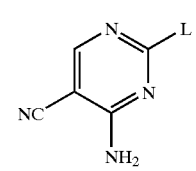

(II)

wherein L is a displaceable group; with an aniline of formula (III):

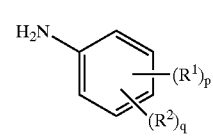

(III)

b) reacting a pyrimidine of formula (IV):

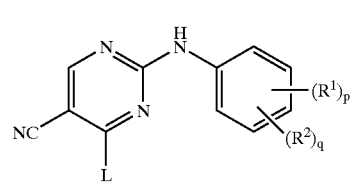

(IV)

wherein L is a displaceable group; with ammonia; or c) reacting a compound of formula (V):

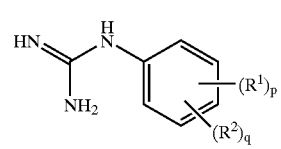

(V)

with a compound of formula (VI):

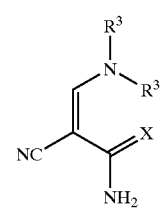

(VI)

wherein X is O or S; R$^3$ is C$_{1-6}$alkyl;

d) reacting a compound of formula (V) with a compound of formula (VII):

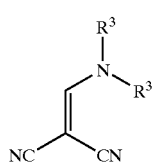

(VII)

e) where $R^2$ is sulphamoyl or a group B-E- and E is —$NHSO_2$—; reacting a pyrimidine of formula (VIII):

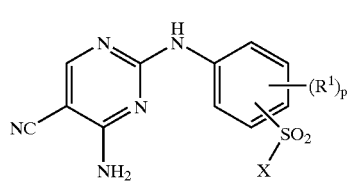

(VIII)

wherein X is a displaceable group; with an amine of formula (IX):

B—$NH_2$ (IX)

and thereafter if necessary:
i) converting a compound of the formula (I) into another compound of the formula (I);
ii) removing any protecting groups;
iii) forming a pharmaceutically acceptable salt or in vivo hydrolysable ester.

L is a displaceable group, suitable values for L are for example, a halogeno or sulphonyloxy group, for example a chloro, bromo, methanesulphonyloxy or toluene-4-sulphonyloxy group.

X is a displaceable group, suitable values for L are for example, a halogeno group, for example a fluoro, chloro or bromo group. Preferably X is fluoro.

Specific reaction conditions for the above reactions are as follows.

a) and b) Pyrimidines of formula (II) and anilines of formula (III) and pyrimidines of formula (IV) and ammonia may be reacted together:
i) in the presence of a suitable solvent for example a ketone such as acetone or an alcohol such as ethanol or butanol or an aromatic hydrocarbon such as toluene or N-methyl pyrrolidine, optionally in the presence of a suitable acid for example an inorganic acid such as hydrochloric acid or sulphuric acid, or an organic acid such as acetic acid or formic acid (or a suitable Lewis acid) and at a temperature in the range of 0° C. to reflux, preferably reflux; or
ii) under standard Buchwald conditions (for example see *J. Am. Chem. Soc.*, 118, 7215; *J. Am. Chem. Soc.*, 119, 8451; *J. Org. Chem.*, 62, 1568 and 6066) for example in the presence of palladium acetate, in a suitable solvent for example an aromatic solvent such as toluene, benzene or xylene, with a suitable base for example an inorganic base such as caesium carbonate or an organic base such as potassium-t-butoxide, in the presence of a suitable ligand such as 2,2'-bis(diphenylphosphino)-1,1'-binaphthyl and at a temperature in the range of 25 to 80° C.

Pyrimidines of the formula (II) and (IV) and anilines of formula (III) are commercially available compounds, or they are known in the literature, or they are prepared by standard processes known in the art.

c) and d) Compounds of formula (V) and compounds of formula (VI) or formula (VII) are reacted together in a suitable solvent such as N-methylpyrrolidinone or butanol at a temperature in the range of 100–200° C., preferably in the range of 150–170° C. The reaction is preferably conducted in the presence of a suitable base such as, for example, sodium methoxide or potassium carbonate.

Compounds of formula (V) and (VI) are commercially available compounds, or they are known in the literature, or they are prepared by standard processes known in the art.

e) Compounds of formula (VIII) and compounds of formula (IX) may be reacted together in the presence of a base for example an inorganic base such as caesium carbonate in the presence of an inert solvent such as toluene or tetrahydrofuran, or in the presence of an organic base such as excess (IX) and at a temperature in the range of 25 to 80° C.

Compounds of formula (VIII) wherein X is fluoro may be prepared according to the following scheme:

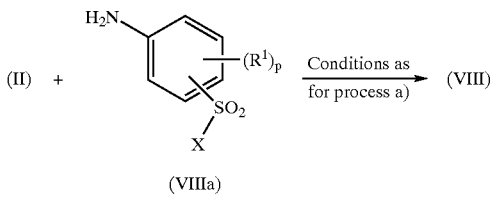

(VIIIa)

Compounds of formula (VIIIa) and (IX) are commercially available compounds, or they are known in the literature, or they are prepared by standard processes known in the art.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

As stated hereinbefore the compounds defined in the present invention possesses anti-cell-proliferation activity such as anti-cancer activity which is believed to arise from the CDK inhibitory activity of the compound. These properties may be assessed, for example, using the procedure set out below:

Assay

The following abbreviations have been used:
HEPES is N-[2-Hydroxyethyl]piperazine-N'-[2-ethanesulfonic acid]
DTT is Dithiothretiol
PMSF is Phenylmethylsulfonyl fluoride The compounds were tested in an in vitro kinase assay in 96 well format using Scintillation Proximity Assay (SPA—obtained from Amersham) for measuring incorporation of [γ-33-P]-Adenosine Triphosphate into a test substrate (GST-Retinoblastoma protein; GST-Rb). In each well was placed the compound to be tested (diluted in DMSO and water to correct concentrations) and in control wells either roscovitine as an inhibitor control or DMSO as a positive control.

Approximately 0.2 µl of CDK2/Cyclin E partially-purified enzyme (amount dependent on enzyme activity) diluted in 25 µl incubation buffer was added to each well then 20 µl of GST-Rb/ATP/ATP33 mixture (containing 0.5 µg GST-Rb and 0.2 µM ATP and 0.14 µCi [γ-33-P]-Adenosine Triphosphate in incubation buffer), and the resulting mixture shaken gently, then incubated at room temperature for 60 minutes.

To each well was then added 150 µL stop solution containing (0.8 mg/well of Protein A-PVT SPA bead (Amersham)), 20 pM/well of Anti-Glutathione Transferase, Rabbit IgG (obtained from Molecular Probes), 61 mM EDTA and 50 mM HEPES pH 7.5 containing 0.05% sodium azide.

The plates were sealed with Topseal-S plate sealers, left for two hours then spun at 2500 rpm, 1124×g., for 5 minutes. The plates were read on a Topcount for 30 seconds per well.

The incubation buffer used to dilute the enzyme and substrate mixes contained 50 mM HEPES pH7.5, 10 mM MnCl$_2$, 1 mM DTT, 100 µM Sodium vanadate, 100 µM NaF, 10 mM Sodium Glycerophosphate, BSA (1 mg/ml final).

Test Substrate

In this assay only part of the retinoblastoma protein (Science 1987 Mar. 13;235(4794):1394–1399; Lee W. H., Bookstein R., Hong F., Young L. J., Shew J. Y., Lee E. Y.) was used, fused to a GST tag. PCR of retinoblastoma gene encoding amino acids 379–928 (obtained from retinoblastoma plasmid ATCC pLRbRNL) was performed, and the sequence cloned into pGEX 2T fusion vector (Smith D. B. and Johnson, K. S. Gene 67, 31 (1988); which contained a tac promoter for inducible expression, internal I$^q$ gene for use in any *E.Coli* host, and a coding region for thrombin cleavage—obtained from Pharmacia Biotech) which was used to amplify amino acids 792–928. This sequence was again cloned into pGEX 2T.

The retinoblastoma 792–928 sequence so obtained was expressed in *E.Coli* (BL21 (DE3) pLysS cells) using standard inducible expression techniques, and purified as follows.

*E.coli* paste was resuspended in 10 ml/g of NETN buffer (50 mM Tris pH 7.5, 120 mM NaCl, 1 mM EDTA, 0.5% v/v NP-40, 1 mM PMSF, 1 ug/ml leupeptin, 1 ug/ml aprotinin and 1 ug/ml pepstatin) and sonicated for 2×45 seconds per 100 ml homogenate. After centrifugation, the supernatant was loaded onto a 10 ml glutathione Sepharose column (Pharmacia Biotech, Herts, UK), and washed with NETN buffer. After washing with kinase buffer (50 mM HEPES pH 7.5, 10 mM MgCl2, 1 mM DTT, 1 mM PMSF, 1 ug/ml leupeptin, 1 ug/ml aprotinin and 1 ug/ml pepstatin) the protein was eluted with 50 mM reduced glutathione in kinase buffer. Fractions containing GST-Rb(792–927) were pooled and dialysed overnight against kinase buffer. The final product was analysed by Sodium Dodeca Sulfate (SDS) PAGE (Polyacrylamide gel) using 8–16% Tris-Glycine gels (Novex, San Diego, USA).

CDK2 and Cyclin E

The open reading frames of CDK2 and Cyclin E were isolated by reverse transcriptase-PCR using HeLa cell and activated T cell mRNA as a template and cloned into the insect expression vector pVL1393 (obtained from Invitrogen 1995 catalogue number: V1392-20). CDK2 and cyclin E were then dually expressed [using a standard virus Baculogold co-infection technique] in the insect SF21 cell system (*Spodoptera Frugiperda* cells derived from ovarian tissue of the Fall Army Worm—commercially available).

Example Production of Cyclin E/CDK2

The following Example provides details of the production of Cyclin E/CDK2 in SF21 cells (in TC100+10% FBS (TCS)+0.2% Pluronic) having dual infection MOI 3 for each virus of Cyclin E & CDK2.

SF21 cells grown in a roller bottle culture to 2.33×10⁶ cells/ml were used to inoculate 10×500 ml roller bottles at 0.2×10E6 cells/ml. The roller bottles were incubated on a roller rig at 28° C.

After 3 days (72 hrs.) the cells were counted, and the average from 2 bottles found to be 1.86×10E6 cells/ml. (99% viable). The cultures were then infected with the dual viruses at an MOI 3 for each virus.

The viruses were mixed together before addition to the cultures, and the cultures returned to the roller rig 28° C.

After 2 days (48 hrs.) post infection the 5 Liters of culture was harvested. The total cell count at harvest was 1.58×10E6 cells/ml.(99% viable). The cells were spun out at 2500 rpm, 30 mins., 4° C. in Heraeus Omnifuge 2.0 RS in 250 ml. lots. The supernatant was discarded.

Partial Co-purification of Cdk2 and Cyclin E

Sf21 cells were resuspended in lysis buffer (50 mM Tris pH 8.2, 10 nm $MgCl_2$, 1 mM DTT, 10 mM glycerophosphate, 0.1 mM sodium orthovanadate, 0.1 mM NaF, 1 mM PMSF, 1 ug/ml leupeptin and 1 ug/ml aprotinin) and homogenised for 2 minutes in a 10 ml Dounce homgeniser. After centrifugation, the supernatant was loaded onto a Poros HQ/M 1.4/100 anion exchange column (PE Biosystems, Hertford, UK). Cdk2 and Cyclin E were coeluted at the beginning of a 0–1M NaCl gradient (run in lysis buffer minus protease inhibitors) over 20 column volumes. Co-elution was checked by western blot using both anti-Cdk2 and anti-Cyclin E antibodies (Santa Cruz Biotechnology, California, US).

By analogy, assays designed to assess inhibition of CDK4 and CDK6 may be constructed. CDK2 (EMBL Accession No. X62071) may be used together with Cyclin A or Cyclin E (see EMBL Accession No. M73812), and further details for such assays are contained in PCT International Publication No. WO99/21845, the relevant Biochemical & Biological Evaluation sections of which are hereby incorporated by reference.

Although the pharmacological properties of the compounds of the formula (I) vary with structural change, in general activity possessed by compounds of the formula (I) may be demonstrated at $IC_{50}$ concentrations or doses in the range 250 μM to 1 nM.

When tested in the above in-vitro assay the CDK2 inhibitory activity of Example 21 was measured as $IC_{50}$=0.033 μM and that of Example 23 as $IC_{50}$=0.017 μM.

The in vivo activity of the compounds of the present invention may be assessed by standard techniques, for example by measuring inhibition of cell growth and assessing cytotoxicity.

Inhibition of cell growth may be measured by staining cells with Sulforhodamine B (SRB), a fluorescent dye that stains proteins and therefore gives an estimation of amount of protein (i.e. cells) in a well (see Boyd, M. R.(1989) Status of the NCI preclinical antitumour drug discovery screen. Prin. Prac Oncol 10:1–12). Thus, the following details are provided of measuring inhibition of cell growth:

Cells were plated in appropriate medium in a volume of 100 ml in 96 well plates; media was Dulbecco's Modified Eagle media for MCF-7, SK-UT-1B and SK-UT-1. The cells were allowed to attach overnight, then inhibitor compounds were added at various concentrations in a maximum concentration of 1% DMSO (v/v). A control plate was assayed to give a value for cells before dosing. Cells were incubated at 37° C.; (5% $CO_2$) for three days.

At the end of three days TCA was added to the plates to a final concentration of 16% (v/v). Plates were then incubated at 4° C. for 1 hour, the supernatant removed and the plates washed in tap water. After drying, 100 ml SRB dye (0.4% SRB in 1% acetic acid) was added for 30 minutes at 37° C. Excess SRB was removed and the plates washed in 1% acetic acid. The SRB bound to protein was solubilised in 10 mM Tris pH7.5 and shaken for 30 minutes at room temperature. The ODs were read at 540 nm, and the concentration of inhibitor causing 50% inhibition of growth was determined from a semi-log plot of inhibitor concentration versus absorbance. The concentration of compound that reduced the optical density to below that obtained when the cells were plated at the start of the experiment gave the value for toxicity.

Typical $IC_{50}$ values for compounds of the invention when tested in the SRB assay are in the range 1 mM to 1 nM.

According to a further aspect of the invention there is provided a pharmaceutical composition which comprises a pyrimidine derivative of the formula (I), or a pharmaceutically acceptable salt or in vivo hydrolysable ester thereof, as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I) will norm ally be administered to a warm-blooded animal at a unit dose within the range 5–5000 mg per square meter body area of the animal, i.e. approximately 0.1–100 mg/kg, and this normally provides a therapeutically-effective dose. A unit dose form such as a tablet or capsule will usually contain, for example 1–250 mg of active ingredient. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a compound of the formula (I), or a pharmaceutically acceptable salt or in vivo hydrolysable ester thereof, as defined hereinbefore for use in a method of treatment of the human or animal body by therapy.

We have found that the compounds defined in the present invention, or a pharmaceutically acceptable salt or in vivo hydrolysable ester thereof, are effective cell cycle inhibitors (anti-cell proliferation agents), which property is believed to arise from their CDK inhibitory properties. Accordingly the compounds of the present invention are expected to be useful in the treatment of diseases or medical conditions mediated alone or in part by CDK enzymes, i.e. the compounds may be used to produce a CDK inhibitory effect in a warm-blooded animal in need of such treatment. Thus the compounds of the present invention provide a method for treating the proliferation of malignant cells characterised by inhibition of CDK enzymes, i.e. the compounds may be used to produce an anti-proliferative effect mediated alone or in part by the inhibition of CDKs. Such a compound of the invention is expected to possess a wide range of anti-cancer properties as CDKs have been implicated in many common human cancers such as leukaemia and breast, lung, colon, rectal, stomach, prostate, bladder, pancreas and ovarian cancer. Thus it is expected that a compound of the invention will possess anti-cancer activity against these cancers. It is in addition expected that a compound of the present invention will possess activity against a range of leukaemias, lymphoid malignancies and solid tumours such as carcinomas and sarcomas in tissues such as the liver, kidney, prostate and pancreas. In particular such compounds of the invention are expected to slow advantageously the growth of primary and recurrent solid tumours of, for example, the colon, breast, prostate, lungs and skin. More particularly such compounds of the invention, or a pharmaceutically acceptable salt or in vivo hydrolysable ester thereof, are expected to inhibit the growth of those primary and recurrent solid tumours which are associated with CDKs, especially those tumours which are significantly dependent on CDKs for their growth and spread, including for example, certain tumours of the colon, breast, prostate, lung, vulva and skin.

It is further expected that a compound of the present invention will possess activity against other cell-proliferation diseases in a wide range of other disease states including leukaemias, fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Thus according to this aspect of the invention there is provided a compound of the formula (I), or a pharmaceutically acceptable salt or in vivo hydrolysable ester thereof, as defined hereinbefore for use as a medicament; and the use of a compound of the formula (I), or a pharmaceutically acceptable salt or in vivo hydrolysable ester thereof, as defined hereinbefore in the manufacture of a medicament for use in the production of a cell cycle inhibitory (anti-cell-proliferation) effect in a warm-blooded animal such as man. Particularly, an inhibitory effect is produced by preventing entry into or progression through the S phase by inhibition of CDK2, CDK4 and/or CDK6, especially CDK2.

According to a further feature of the invention, there is provided a compound of the formula (I), or a pharmaceutically acceptable salt or in vivo hydrolysable ester thereof, as defined here before in the manufacture of a medicament for use in the treatment of cancers (solid tumours and leukaemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation, particularly in the treatment of cancers.

According to a further feature of this aspect of the invention there is provided a method for producing a cell cycle inhibitory (anti-cell-proliferation) effect in a warm-blooded animal, such as man, in need of such treatment which comprises administering to said animal an effective amount of a compound as defined immediately above. Particularly, an inhibitory effect is produced by preventing entry into or progression through the S phase by inhibition of CDK1, CDK4 and/or CDK6, especially CDK2.

According to a further feature of this aspect of the invention there is provided a method for producing a cell cycle inhibitory (anti-cell-proliferation) effect in a warm-blooded animal, such as man, in need of such treatment which comprises administering to said animal an effective amount of a compound as defined immediately above or a pharmaceutically acceptable salt or in vivo hydrolysable ester thereof. Particularly, an inhibitory effect is produced by preventing entry into or progression through the S phase by inhibition of CDK2, CDK4 and/or CDK6, especially CDK2.

According to an additional feature of this aspect of the invention there is provided a method of treating cancers in a warm-blooded animal, such as man, in need of such treatment which comprises administering to said animal an effective amount of a compound as defined immediately above or a pharmaceutically acceptable salt or in vivo hydrolysable ester thereof.

As stated above the size of the dose required for the therapeutic or prophylactic treatment of a particular cell-proliferation disease will necessarily be varied depending on the host treated, the route of administration and the severity of the illness being treated. A unit dose in the range, for example, 1–100 mg/kg, preferably 1–50 mg/kg is envisaged.

The CDK inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the cell cycle inhibitory treatment defined hereinbefore may be: surgery, radiotherapy or chemotherapy. Such chemotherapy may cover three main categories of therapeutic agent:

(i) other cell cycle inhibitory agents that work by the same or different mechanisms from those defined hereinbefore;

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, anti-androgens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincrisitine and taxoids like taxol, taxotere); topoisomerase inhibitors (for example epipodophyllotoxins like etoposide and teniposide, amsacrine, topotecan). According to this aspect of the invention there is provided a pharmaceutical product comprising a compound of the formula (I) as defined hereinbefore and an additional anti-tumour substance as defined hereinbefore for the conjoint treatment of cancer.

In addition to their use in therapeutic medicine, the compounds of formula (I) and their pharmaceutically acceptable salts are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

In the above other pharmaceutical composition, process, method, use and medicament manufacture features, the alternative and preferred embodiments of the compounds of the invention described herein also apply.

EXAMPLES

The invention will now be illustrated by the following non-limiting examples in which, unless stated otherwise:
(i) temperatures are given in degrees Celsius (° C.); operations were carried out at room or ambient temperature, that is, at a temperature in the range of 18–25° C.;
(ii) organic solutions were dried over anhydrous magnesium sulphate; evaporation of solvent was carried out using a rotary evaporator under reduced pressure (600–4000 Pascals; 4.5–30 mmHg) with a bath temperature of up to 60° C.;
(iii) chromatography means flash chromatography on silica gel; thin layer chromatography (TLC) was carried out on silica gel plates;
(iv) in general, the course of reactions was followed by TLC and reaction times are given for illustration only;
(v) final products had satisfactory proton nuclear magnetic resonance (NMR) spectra and/or mass spectral data;
(vi) yields are given for illustration only and are not necessarily those which can be obtained by diligent process development; preparations were repeated if more material was required;
(vii) when given, NMR data is in the form of delta values for major diagnostic protons, given in parts per million (ppm) relative to tetramethylsilane (TMS) as an internal standard, determined at 300 MHz using perdeuterio dimethyl sulphoxide (DMSO-$d_6$) as solvent unless otherwise indicated;
(viii) chemical symbols have their usual meanings; SI units and symbols are used;
(ix) solvent ratios are given in volume:volume (v/v) terms; and
(x) mass spectra were run with an electron energy of 70 electron volts in the chemical ionization (CI) mode using a direct exposure probe; where indicated ionization was effected by electron impact (EI), fast atom bombardment (FAB) or electrospray (ESP); values for m/z are given; generally, only ions which indicate the parent mass are reported;
(xi) unless stated otherwise compounds containing an asymmetrically substituted carbon and/or sulphur atom have not been resolved;
(xii) where a synthesis is described as being analogous to that described in a previous example the amounts used are the millimolar ratio equivalents to those used in the previous example;
(xvi) the following abbreviations have been used:
  NMP 1-methyl-2-pyrrolidinone; and
  DMSO dimethylsulphoxide.

Example 1

4-Amino-5-cyano-2-(4-sulphamoylanilino) pyrymidine

A solution of 4-amino-2-chloro-5-cyanopyrimidine (0.5 g, 3.24 mmol) and 4-sulphamoylaniline (0.58 g, 3.4 mmol) in NMP (2 ml) was heated at 80° C. for 20 hours. The mixture was allowed to cool and was diluted with water. The resulting precipitate was collected by filtration, washed with water and dried under vacuum at 60° C. to give the title compound (889 mg, 95%). NMR: 7.08 (s, 2H), 7.60 (s, 2H), 7.67 (d, 2H), 7.95 (d, 2H), 8.40 (s, 1H), 10.03 (s, 1H); m/z 291 $(MH)^+$.

Example 2

4-Amino-5-cyano-2-{4-[N-(3-dimethylaminopropyl) sulphamoyl]anilino}pyrimidine

3-Dimethylaminopropylamine (3 ml) was added to 4-amino-5-cyano-2-(4-fluorosulphonylanilino)pyrimidine (Method 1; 250 mg, 0.853 mmol), the mixture was heated at 90° C. for 45 minutes then stirred at ambient temperature for 18 hours. The volatiles were removed by evaporation and residue was purified by chromatography on silica gel eluting with ethyl acetate/hexane/methanol (50:50:0) increasing in polarity to (80:0:20). The product was triturated with ether and a few drops of methanol and the resulting solid collected by filtration to give the title compound (176 mg, 55%). NMR: 1.45 (t, 2H), 2.04 (s, 6H), 2.10 (t, 2H), 2.72 (t, 2H), 7.60 (s, 2H), 7.62 (d, 2H), 7.98 (d, 2H), 8.40 (s, 1H); m/z 376 $(MH)^+$.

Examples 3–20

Following the procedure of Example 2 and using 4-amino-5-cyano-2-(4-fluorosulphonylanilino)pyrimidine (Method 1) and the appropriate amine the following compounds were prepared.

| Ex | Compound | NMR | m/z $(MH)^+$ |
|---|---|---|---|
| 3[1] | 4-Amino-5-cyano-2-{4-[N-(2-piperidinoethyl)sulphamoyl]anilino}pyrimidine | 1.30–1.48 (m, 6H), 2.19–2.28 (m, 6H), 2.78 (t, 2H), 7.60 (s, 2H), 7.64 (d, 2H), 7.98 (d, 2H), 8.40 (s, 1H) | 402 |
| 4[1] | 4-Amino-5-cyano-2-(4-{N-[2-(1-methylpyrrolidin-2-yl)ethyl]sulphamoyl}anilino)pyrimidine | 1.18–1.30 (m, 2H), 1.45–1.80 (m, 4H), 1.9–2.0 (m, 2H), 2.10 (s, 3H), 2.67–2.75 (m, 2H), 2.85 (m, 1H), 7.61 (s, 2H), 7.64 (d, 2H), 8.00 (d, 2H), 8.42 (s, 1H) | 402 |
| 5[1] | 4-Amino-5-cyano-2-{4-[N-(2-isopropylaminoethyl)sulphamoyl]anilino}pyrimidine | 0.86 (d, 6H), 2.50 (m, 2H), 2.59 (m, 1H), 2.78 (t, 2H), 7.60 (s, 2H), 7.62 (d, 2H), 8.00 (d, 2H), 8.40 (s, 1H), 10.25 (s, 1H) | 376 |

-continued

| Ex | Compound | NMR | m/z (MH)+ |
|---|---|---|---|
| 6[1] | 4-Amino-5-cyano-2-{4-[N-(3-isopropylaminopropyl)sulphamoyl]anilino}pyrimidine | 0.89 (d, 6H), 1.42 (m, 2H), 2.40 (t, 2H), 2.58 (m, 1H), 2.75 (t, 2H), 7.60 (s, 2H), 7.62 (d, 2H), 7.98 (d, 2H), 8.40 (s, 1H) | 390 |
| 7[1] | 4-Amino-5-cyano-2-{4-[N-(2-methoxyethyl)sulphamoyl]anilino}pyrimidine | 2.84 (t, 2H), 3.15 (s, 3H), 3.28 (t, 2H), 7.60 (s, 2H), 7.65 (d, 2H), 7.96 (d, 2H), 8.40 (s, 1H) | 349 |
| 8[1] | 4-Amino-5-cyano-2-{4-[N-(3-methoxypropyl)sulphamoyl]anilino}pyrimidine | 1.56 (m, 2H), 2.73 (t, 2H), 3.12 (s, 3H), 3.24 (t, 2H), 7.60 (s, 2H), 7.62 (d, 2H), 7.98 (d, 2H), 8.40 (s, 1H) | 363 |
| 9[1] | 4-Amino-5-cyano-2-{4-[N-(3-isopropoxypropyl)sulphamoyl]anilino}pyrimidine | 0.99 (d, 6H), 1.53 (m, 2H), 2.72 (t, 2H), 3.28 (t, 2H), 3.40 (br s, 1H), 7.35 (s, 1H), 7.60 (s, 2H), 7.62 (d, 2H), 7.98 (d, 2H), 8.40 (s, 1H) | 391 |
| 10[1] | 4-Amino-5-cyano-2-{4-[N-(3-ethoxypropyl)sulphamoyl]anilino}pyrimidine | 1.02 (t, 3H), 1.58 (q, 2H), 2.75 (t, 2H), 3.24–3.32 (m, 4H), 7.38 (s, 1H), 7.60 (s, 2H), 7.62 (d, 2H), 7.98 (d, 2H), 8.40 (s, 1H) | 377 |
| 11[1] | 4-Amino-5-cyano-2-{4-[N-(tetrahydrofur-2-ylmethyl)sulphamoyl]anilino}pyrimidine | 1.46–1.52 (m, 1H), 1.68–1.83 (m, 3H), 2.72 (d, 2H), 3.55 (m, 1H), 3.64 (m, 1H), 3.78 (m, 1H), 7.51 (s, 1H), 7.60 (s, 2H), 7.64 (d, 2H), 7.98 (d, 2H), 8.40 (s, 1H) | 375 |
| 12[1] | 4-Amino-5-cyano-2-{4-[N-(2-pyrid-2-ylethyl)sulphamoyl]anilino}pyrimidine | 2.82 (m, 2H), 3.10 (t, 2H), 7.15–7.22 (m, 3H), 7.60–7.68 (m, 4H), 7.95 (d, 2H), 8.39–8.42 (m, 2H) | 394 |
| 13[1] | 4-Amino-5-cyano-2-(4-{N-[3-(2-oxopyrrolidin-1-yl)propyl]sulphamoyl}anilino)pyrimidine | 1.46–1.58 (m, 2H), 1.8–1.9 (m, 2H), 2.15 (t, 2H), 2.66 (t, 2H), 3.10 (t, 2H), 3.20 (t, 2H), 5.98 (s, 2H), 7.61 (d, 2H), 7.98 (d, 2H), 8.40 (s, 1H) | 416 |
| 14[1] | 4-Amino-5-cyano-2-{4-[N-(3-morpholinopropyl)sulphamoyl]anilino}pyrimidine | 1.50 (t, 2H), 2.15–2.20 (m, 6H), 2.72 (t, 2H), 3.48 (t, 4H), 7.60 (s, 2H), 7.62 (d, 2H), 7.98 (d, 2H), 8.40 (s, 1H) | 418 |
| 15[1] | 4-Amino-5-cyano-2-{4-[N-(3-imidazol-1-ylpropyl)sulphamoyl]anilino}pyrimidine | 1.7–1.8 (m, 2H), 2.62 (t, 2H), 3.94 (t, 2H), 6.85 (s, 1H), 7.08 (s, 1H), 7.50 (s, 1H), 7.58–7.64 (m, 4H), 7.98 (d, 2H), 8.40 (s, 1H) | 399 |
| 16[1,2] | 4-Amino-5-cyano-2-[4-(N-pentylsulphamoyl)anilino]pyrimidine | 0.80 (t, 3H), 1.11–1.2 (m, 4H), 1.35 (m, 2H), 2.65 (m, 2H), 7.35 (t, 1H), 7.59 (s, 2H), 7.62 (d, 2H), 7.98 (d, 2H), 8.40 (s, 1H) | 361 |
| 17[1,2] | 4-Amino-5-cyano-2-[4-(N-allylsulphamoyl)anilino]pyrimidine | 3.35 (t, 2H), 5.00 (d, 1H), 5.10 (d, 1H), 5.65 (m, 1H), 7.60 (m, 3H), 7.64 (d, 2H), 7.98 (d, 2H), 8.40 (s, 1H) | 331 |
| 18[1,2] | 4-Amino-5-cyano-2-{4-[N-(4-hydroxyphenethyl)sulphamoyl]anilino}pyrimidine | 2.50–2.58 (m, 2H), 2.82 (m, 2H), 6.61 (d, 2H), 6.90 (d, 2H), 7.48 (t, 1H), 7.60 (s, 2H), 7.62 (d, 2H), 7.98 (d, 2H), 8.40 (s, 1H), 9.12 (s, 1H) | 411 |
| 19[1,2] | 4-Amino-5-cyano-2-{4-[N-(4-fluorobenzyl)sulphamoyl]anilino}pyrimidine | 3.92 (s, 2H), 7.08 (dd, 2H), 7.24 (dd, 2H), 7.60 (s, 2H), 7.64 (d, 2H), 7.98 (d, 2H), 8.40 (s, 1H) | 397 (M-H)− |
| 20[1,2] | 4-Amino-5-cyano-2-{4-[N-(phenethyl)sulphamoyl]anilino}pyrimidine | 2.66 (t, 2H), 2.90 (t, 2H), 7.10–7.26 (m, 5H), 7.58 (s, 2H), 7.62 (d, 2H), 7.98 (d, 2H), 8.40 (s, 1H) | 393 (M-H)− |

[1]Reaction mixture was heated at 95° C. for 2 hours
[2]Chromatography eluent was ethyl acetate/hexane (50:50) increasing in polarity to (100:0)

Example 21

4-Amino-5-cyano-2-{4-[N-(cyclobutyl)sulphamoyl]anilino}pyrimidine

Cyclobutylamine (2 ml) was added to 4-amino-5-cyano-2-(4-fluorosulphonylanilino) pyrimidine (Method 1; 250 mg, 0.853 mmol), the mixture was heated at 40° C. for 1 hour and then stirred at ambient temperature for 18 hours. The volatiles were removed by evaporation and residue was purified by chromatography on silica gel eluting with ethyl acetate/hexane (50:50). The product was triturated with ether/hexane and the resulting solid collected by filtration to give the title compound (91 mg, 31%). NMR: 1.41–1.50 (m, 2H); 1.62–1.78 (m, 2H); 1.82–1.90 (m, 2H); 3.59 (m, 1H); 7.60 (s, 2H); 7.62 (d, 2H); 7.98 (d, 2H); 8.40 (s, 1H); m/z: 345 (MH)+.

Examples 21–27

Following the procedure of Example 21 and using 4-amino-5-cyano-2-(4-fluorosulphonylanilino)pyrimidine (Method 1) and the appropriate amine the following compounds were prepared.

| Ex | Compound | NMR | m/z (MH)+ |
|---|---|---|---|
| 22 | 4-Amino-5-cyano-2-{4-[N-(cyclopropyl)sulphamoyl]anilino}pyrimidine | 1.41–1.50 (m, 2H); 1.62–1.78 (m, 2H); 1.82–1.90 (m, 2H); 3.59 (m, 1H); 7.60 (s, 2H); 7.62 (d, 2H); 7.98 (d, 2H); 8.40 (s, 1H) | 331 |
| 23 | 4-Amino-5-cyano-2-[4-(N-propylsulphamoyl)anilino]pyrimidine | 0.78 (t, 3H); 1.35 (m, 2H); 2.64 (m, 2H); 7.38 (t, 1H); 7.60 (s, 2H); 7.62 (d, 2H); 7.98 (d, 2H); 8.40 (s, 1H) | 333 |
| 24 | 4-Amino-5-cyano-2-{4-[N-(2,2,2-trifluoroethyl)sulphamoyl]anilino}pyrimidine | 3.62 (q, 2H); 7.60 (s, 2H); 7.70 (d, 2H); 7.98 (d, 2H); 8.40 (s, 1H) | 373 |
| 25 | 4-Amino-5-cyano-2-{4-[N-(3-methoxybenzyl)sulphamoyl]anilino}pyrimidine | 3.65 (s, 3H); 3.92 (s, 2H); 6.72–6.80 (m, 3H); 7.18 (t, 1H); 7.60 (s, 2H); 7.64 (d, 2H); 7.98 (d, 2H); 8.40 (s, 1H) | 409 (M-H)− |
| 26 | 4-Amino-5-cyano-2-{4-[N-(cyclopropylmethyl)sulphamoyl]anilino}pyrimidine | 0.01–0.05 (m, 2H); 0.27–0.32 (m, 2H); 0.69–0.79 (m, 1H); 2.58 (t, 2H); 7.50 (t, 1H); 7.58 (s, 2H); 7.60 (d, 2H); 7.92 (d, 2H); 8.39 (s, 1H) | 345 |
| 27 | 4-Amino-5-cyano-2-{4-[N-(4-methoxyphenethyl)sulphamoyl]anilino}pyrimidine | 2.58 (t, 2H); 2.86 (t, 2H); 3.70 (s, 3H); 6.80 (d, 2H); 7.04 (d, 2H); 7.59 (s, 2H); 7.61 (d, 2H); 7.98 (d, 2H); 8.40 (s, 1H) | 423 (M-H)− |

Example 28

4-Amino-5-cyano-2-{4-[N-(3-imidazol-1-ylpropyl)carbamoyl]anilino}pyrimidine

A solution of 4-amino-2-chloro-5-cyanopyrimidine (200 mg, 1.3 mmol) and 4-[N-(3-imidazol-1-ylpropyl)carbamoyl]aniline (Method 3; 633 mg, 2.6 mmol) in NMP (10 ml) was heated at 120° C. for 48 hours. The mixture was allowed to cool, was diluted with water and extracted with ethyl acetate. The organic extracts were combined, dried and the solvent removed by evaporation, the residue was triturated with ether/hexane and the product collected by filtration to give the title compound (10 mg, 2%). NMR: 1.92 (q, 2H) 3.20 (q, 2H), 4.00 (t, 2H), 6.87 (s, 1H), 7.19 (s, 1H), 7.55 (s, 2H), 7.62 (s, 1H), 7.86 (d, 2H), 8.32 (t, 1H), 8.38 (s,1H), 9.90 (s, 1H); m/z 363 (MH)+.

Example 29

4-Amino-5-cyano-2-{4-[N-(2-N,N-dimethylaminoethyl)sulphamoyl]anilino}pyrimidine

2-Dimethylaminoethylamine (2 ml) was added to 4-amino-5-cyano-2-(4-fluorosulphonylanilino)pyrimidine (Method 1; 250 mg, 0.853 mmol) and the mixture was stirred at ambient temperature for 2 hours. The volatiles were removed by evaporation and residue was purified by chromatography eluting with ethyl acetate/hexane/methanol (50:50:0) increasing in polarity to (95:0:5). The product was triturated with ether and collected by filtration to give the title compound (110 mg, 36%). NMR: 2.05 (s, 6H), 2.20 (t, 2H), 9.78 (t, 2H), 7.68–7.70 (m, 3H); 7.98 (d, 2H), 8.40 (s, 1H); m/z 362 (MH)+.

Example 30

4-Amino-5-cyano-2-{4-[N-(3-hydroxy-2,2-dimethylpropyl)sulphamoyl]anilino}pyrimidine A solution of 4-amino-2-chloro-5-cyanopyrimidine (150 mg, 0.97 mmol), 4-[N-(3-hydroxy-2,2-dimethylpropyl)sulphamoyl]aniline (Method 4; 274 mg, 1.07 mmol) in NMP (5 ml) was heated at 120° C. for 24 hours. The mixture was allowed to cool, was diluted with water and extracted with ethyl acetate. The organic extracts were combined, dried and the solvent removed by evaporation, the residue was triturated with ether and the product collected by filtration to give the title compound (187 mg, 52%). NMR: 0.72 (s, 6H), 2.52 (d, 2H), 3.08 (d, 2H), 4.40 (t, 1H), 7.19 (t, 1H), 7.60 (s, 1H), 7.64 (d, 2H), 7.96 (d, 2H), 8.40 (s, 1H); m/z 375 (M−H)−.

Example 31

4-Amino-5-cyano-2-(3-chloroanilino)pyrimidine

3-Chloroaniline (277 mg, 2.2 mmol) was treated with 4-amino-2-chloro-5-cyanopyrimidine (0.3 g, 2.0 mmol) by the procedure described in Example 1 to give the title compound (430 mg, 90%). NMR: 7.00 (d, 1H), 7.28 (dd, 1H), 7.55 (s, 2H), 7.70 (d, 1H), 7.89 (s, 1H), 8.38 (s, 1H), 9.81 (s, 1H); m/z 246 (MH)+.

Preparation of Starting Materials

The starting materials for the Examples above are either commercially available or are readily prepared by standard methods from known materials. For example the following reactions are illustrations but not limitations of the preparation of some of the starting materials used in the above reactions.

Method 1

4-Amino-5-cyano-2-(4-fluorosulphonylanilino)pyrimidine

A solution of 4-amino-2-chloro-5-cyanopyrimidine (8.0 g, 52 mmol) and sulphanilyl fluoride (9.07 g, 52 mmol) in NMP (155 ml) was heated at 120° C. for 24 hours. The mixture was allowed to cool and was diluted with water. The resulting precipitate was collected by filtration, washed with water and dried under vacuum at 60° C. for 2 hours. The crude product was recrystallized from ethyl acetate/hexane to give the title compound (5.45 g, 37%). NMR: 7.70 (s, 24H), 7.93 (d, 2H), 8.15 (d, 2H), 8.45 (s, 1H); m/z: 292 (MH)+.

Method 2

4-[N-(3-imidazol-1-ylpropyl)carbamoyl]nitrobenzene

A solution of 1-(3-aminopropyl)imidazole (3.87 ml, 33 mmol) in ethanol (65 ml) was added to 4-nitrobenzoyl chloride (4.0 g, 22 mmol) and the mixture stirred at ambient temperature for 24 hours. The volatiles were removed by evaporation and the residue was dissolved in ethyl acetate, washed with water and dried. The solvent was removed by evaporation, the residue was triturated with hexane and the product collected by filtration to give the title compound (3.2 g, 55%). NMR: 1.98 (t, 2H), 3.24 (q, 2H), 4.01 (t, 2H), 6.87 (s, 1H), 7.19 (s, 1H), 7.64 (s, 2H), 8.15 (d, 2H), 8.30 (d, 2H); 8.80 (t, 1H); m/z 275 (MH)$^+$.

Method 3

4-[N-(3-imidazol-1-ylpropyl)carbamoyl]aniline

10% Palladium on carbon (500 mg) was added to a solution of 4-[N-(imidazol-1-ylpropyl)carbamoyl] nitrobenzene (Method 2; 3.0 g, 11 mmol) dissolved in ethanol (200 ml) and ethyl acetate (50 ml). The mixture was stirred under hydrogen for 2 hours, the catalyst removed by filtration through diatomaceous earth and the filter pad washed through with methanol. The solvent was removed from the filtrate by evaporation to give the title compound (1.5 g, 57%). NMR: 1.91 (t, 2H), 3.19 (q, 2H), 3.98 (t, 2H), 5.58 (s, 2H), 6.52 (d, 2H), 6.86 (s, 1H), 7.19 (s, 1H), 7.58 (d, 2H), 7.62 (s, 1H); 8.00 (t, 1H); m/z 245 (MH)$^+$.

Method 4

4-[N-(3-hydroxy-2,2-dimethylpropyl)sulphamoyl] aniline

A mixture of sulphanilyl fluoride (1 g, 5.7 mmol), 3-amino-2,2-dimethylpropan-1-ol (884 mg, 8.6 mmol) and triethylamine (0.876 ml, 6.3 mmol) in butan-1-ol (20 ml) was heated at reflux for 24 hours. The volatiles were removed by evaporation and residue was purified by chromatography on silica gel to give the title compound. NMR: 0.72 (s, 6H), 2.52 (d, 2H), 3.08 (d, 2H), 4.40 (t, 1H), 7.19 (t, 1H), 7.60 (s, 1H), 7.64 (d, 2H), 7.96 (d, 2H), 8.40 (s, 1H), m/z 259 (MN)$^+$.

Example 32

The following illustrate representative pharmaceutical dosage forms containing the compound of formula (I), or a pharmaceutically acceptable salt or in vivo hydrolysable ester thereof (hereafter compound X), for therapeutic or prophylactic use in humans:

| (a): Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b): Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c): Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d): Capsule | mg/capsule |
|---|---|
| Compound X | 10 |
| Lactose Ph.Eur | 488.5 |
| Magnesium stearate | 1.5 |

| (e): Injection I | (50 mg/ml) |
|---|---|
| Compound X | 5.0% w/v |

| (e): Injection I | (50 mg/ml) |
|---|---|
| 1 M Sodium hydroxide solution | 15.0% v/v |
| 0.1 M Hydrochloric acid | (to adjust pH to 7.6) |
| Polyethylene glycol 400 | 4.5% w/v |
| Water for injection | to 100% |

| (f): Injection II | 10 mg/ml |
|---|---|
| Compound X | 1.0% w/v |
| Sodium phosphate BP | 3.6% w/v |
| 0.1 M Sodium hydroxide solution | 15.0% v/v |
| Water for injection | to 100% |

| (g): Injection III | (1 mg/ml, buffered to pH 6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

Note

The above formulations may be obtained by conventional procedures well known in the pharmaceutical art. The tablets (a)–(c) may be enteric coated by conventional means, for example to provide a coating of cellulose acetate phthalate.

What is claimed is:

1. A compound of formula (I):

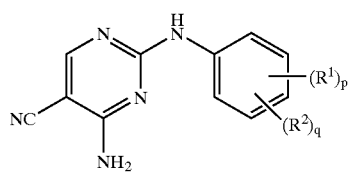

wherein:
R$^1$ is halo, nitro, cyano, hydroxy, amino, carboxy, carbamoyl, mercapto, C$_{1-6}$alkyl, C$_{2-6}$alkenyl or C$_{2-6}$alkynyl;
p is 0–4; wherein the values of R$^1$ may be the same or different;
R$^2$ is sulphamoyl or a group B-E-; wherein
B is selected from C$_{1-6}$alkyl, C$_{2-6}$alkenyl, C$_{2-6}$alkynyl, C$_{3-8}$cycloalkyl, C$_{3-8}$cycloalkylC$_{1-6}$alkyl, phenyl, a heterocyclic group, phenylC$_{1-6}$alkyl or (heterocyclic group)C$_{1-6}$alkyl; wherein said C$_{1-6}$alkyl, C$_{2-6}$alkenyl, C$_{2-6}$alkynyl, C$_{3-8}$cycloalkyl, C$_{3-8}$cycloalkylC$_{1-6}$alkyl, phenyl, heterocyclic group, phenylC$_{1-6}$alkyl or (heterocyclic group)C$_{1-6}$alkyl are optionally substituted on carbon by one or more D; and wherein if said heterocyclic group contains an —NH— moiety that nitrogen may be optionally substituted by a group selected from G;
E is —C(O)—, —N(R$^a$)C(O)—, —C(O)N(R$^a$)—, —S(O)$_r$—, —SO$_2$N(R$^a$)— or —N(R$^a$)SO$_2$—; wherein R$^a$ is hydrogen or C$_{1-6}$alkyl optionally substituted by one or more D and r is 1–2;
D is independently selected from halo, nitro, cyano, hydroxy, trifluoromethyl, trifluoromethoxy, amino, carboxy, carbamoyl, mercapto, sulphamoyl, C$_{1-6}$alkyl, C$_{2-6}$alkenyl, C$_{2-6}$alkynyl, C$_{1-6}$alkoxy, C$_{1-6}$alkanoyl, C$_{1-6}$alkanoyloxy, N-(C$_{1-6}$alkyl)amino, N,N-(C$_{1-6}$alkyl)$_2$amino, C$_{1-6}$alkanoylamino, N-(C$_{1-6}$alkyl)carbamoyl, N,N-(C$_{1-6}$alkyl)$_2$carbamoyl, C$_{1-6}$alkylS(O)$_a$ wherein a is 0 to 2, C$_{1-6}$alkoxycarbonyl, N-(C$_{1-6}$alkyl)sulphamoyl and N,N-(C$_{1-6}$alkyl)$_2$sulphamoyl;
G is selected from C$_{1-4}$alkyl, C$_{1-4}$alkanoyl, C$_{1-4}$alkylsulphonyl, C$_{1-4}$alkyoxycarbonyl, carbamoyl, N-(C$_{1-4}$alkyl)carbamoyl, N,N-(C$_{1-4}$alkyl)carbamoyl, benzyl, beuzyloxycarbonyl, benzoyl and phenylsulphonyl; and
q is 0–2; wherein the values of R$^2$ maybe the same or different; and wherein p+q=1–5;
with the proviso that that compound is not 2-(2,4-dimethylanilino)-4-amino-5-cyanopyrimidine;
or a pharmaceutically acceptable salt thereof.

2. A compound of formula (I) as claimed in claim 1 wherein R$^1$ is chloro; or a pharmaceutically acceptable salt thereof.

3. A compound of formula (I) as claimed in claim 1 wherein p is 0 or 1; or a pharmaceutically acceptable salt thereof.

4. A compound of formula (I) as claimed in claim 1 wherein R$^2$ is sulphamoyl or a group B-E-; wherein
B is selected from C$_{1-6}$alkyl, C$_{2-6}$alkenyl, C$_{3-8}$cycloalkyl, C$_{3-8}$cycloalkylC$_{1-6}$alkyl, phenylC$_{1-6}$alkyl or (heterocyclic group)C$_{1-6}$alkyl; wherein said C$_{1-6}$alkyl, C$_{2-6}$alkenyl, C$_{3-8}$cycloalkyl, C$_{3-8}$cycloalkylC$_{1-6}$alkyl, phenylC$_{1-6}$alkyl or (heterocyclic group)C$_{1-6}$alkyl are optionally substituted on carbon by one or more D; and wherein if said heterocyclic group contains an —NH— moiety that nitrogen may be optionally substituted by a group selected from G;
E is —N(R$^a$)SO$_2$— or —N(R$^a$)C(O)—; wherein R$^a$ is hydrogen;
D is independently selected from halo, hydroxy, C$_{1-6}$alkoxy or N-(C$_{1-6}$alkyl)amino, N,N-(C$_{1-6}$alkyl)$_2$amino; and
G is C$_{1-4}$alkyl;
or a pharmaceutically acceptable salt thereof.

5. A compound of formula (I) as claimed in claim 1 wherein R$^2$ is selected from sulphamoyl, N-(cyclopropylmethyl)sulphamoyl, N-(tetrahydrofur-2-ylmethyl)sulphamoyl, N-(2-methoxyethyl)sulphamoyl, N-(2-pyrid-2-ylethyl)sulphamoyl, N-(2-piperidin-1-ylethyl)sulphamoyl, N-[2-(1-methylpyrrolidin-2-yl)ethyl]sulphamoyl, N-(2-isopropylaminoethyl)sulphamoyl, N-(2,2,2-trifluoroethyl)sulphamoyl, N-(2-dimethylaminoethyl)sulphamoyl, N-(3-methoxypropyl)sulphamoyl, N-(3-ethoxypropyl)sulphamoyl, N-(3-isopropoxypropyl)sulphamoyl, N-(3-dimethylaminopropyl)sulphamoyl, N-[3-(2-oxopyrrolidin-1-yl)propyl]sulphamoyl, N-(3-morpholinopropyl)sulphamoyl, N-(3-imidazol-1-ylpropyl)sulphamoyl, N-(3-isopropylaminopropyl)sulphamoyl, N-(propyl)sulphamoyl, N-(3-hydroxy-2,2-dimethylpropyl)sulphamoyl, N-(pentyl)sulphamoyl, N-(allyl)sulphamoyl, N-(cyclopropyl)sulphamoyl, N-(cyclobutyl)sulphamoyl, N-(3-methoxybenzyl)sulphamoyl, N-(4-fluorobenzyl)sulphamoyl, N-(phenethyl)sulphamoyl, N-(4-hydroxyphenethyl)sulphamoyl, N-(4-methoxyphenethyl)sulphamoyl and N-(3-imidazol-1-ylpropyl)carbamoyl; or a pharmaceutically acceptable salt thereof.

6. A compound of formula (I) as claimed in claim 1 wherein q is 0 or 1; or a pharmaceutically acceptable salt thereof.

7. A compound of formula (I) as claimed in claim 1 wherein p+q is 1; or a pharmaceutically acceptable salt thereof.

8. A compound of formula (I) as claimed in claim 1 selected from:
4-amino-5-cyano-2-{4-[N-(2-methoxyethyl)sulphamoyl]anilino}pyrimidine;
4-amino-5-cyano-2-{4-[N-(tetrahydrofur-2-ylmethyl)sulphamoyl]anilino}pyrimidine;
4-amino-5-cyano-2-{4-[N-(4-fluorobenzyl)sulphamoyl]anilino}pyrimidine;
4-amino-5-cyano-2-{4-[N-(3-methoxypropyl)sulphamoyl]anilino}pyrimidine;
4-amino-5-cyano-2-{4-[N-(cyclopropyl)sulphamoyl]anilino}pyrimidine;
4-amino-5-cyano-2-[4-(N-allylsulphamoyl)anilino]pyrimidine;
4-amino-5-cyano-2-[4-(N-propysulphamoyl)anilino]pyrimidine;
4-amino-5-cyano-2-{4-[N-(2-isopropylaminoethyl)sulphamoyl]anilino}pyrimidine;
4-amino-5-cyano-2-{4-[N-(3-isopropylaminopropyl)sulphamoyl]anilino}pyrimidine; and
4-amino-5-cyano-2-{4-[N-(2-piperidinoethyl)sulphamoyl]anilino}pyrimidine;
or a pharmaceutically acceptable salt thereof.

9. A process for preparing a compound of formula (I) or a pharmaceutically acceptable salt thereof which process (wherein R$^2$, R$^2$, p and q are, unless otherwise specified, as defined in claim 1) comprises of:

a) reaction of a pyrimidine of formula (II):

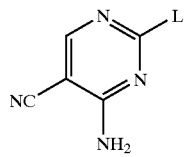
(II)

wherein L is a displaceable group; with an aniline of formula (III);

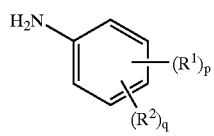
(III)

b) reacting a pyrimidine of formula (IV):

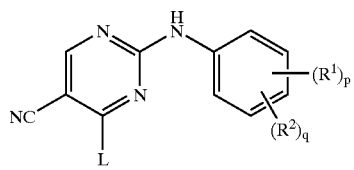
(IV)

wherein L is a displaceable group; with ammonia; or c) reacting a compound of formula (V):

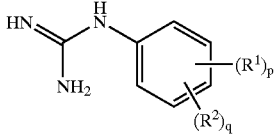
(V)

with a compound of formula (VI):

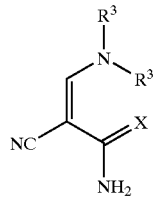
(VI)

wherein X is O or S; $R^3$ is $C_{1-6}$alkyl;

d) reacting a compound of formula (V) with a compound of formula (VII):

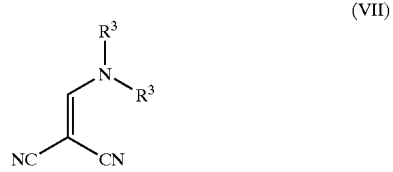
(VII)

e) where $R^2$ is sulphamoyl or a group B-E- and E is —$NHSO_2$—; reacting a pyrimidine of formula (VIII):

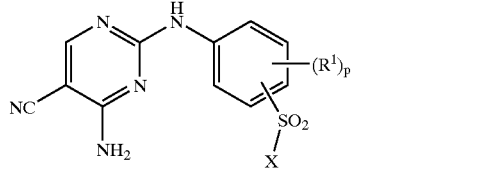
(VIII)

wherein X is a displaceable group; with an amine of formula (IX):

B—$NH_2$     (IX)

and thereafter optionally:

i) converting a compound of the formula (I) into another compound of the formula (I);

ii) removing any protecting groups;

iii) forming a pharmaceutically acceptable salt.

10. A pharmaceutical composition which comprises a compound of the formula (I), or a pharmaceutically acceptable salt thereof, as claimed in any one of claims 1–8, in association with a pharmaceutically-acceptable diluent or carrier.

11. A method for inhibiting a CDK2, CDK4 or CDK6 cell cycle kinase in a warm-blooded animal in need thereof, which comprises administering to said animal an effective amount of a compound of formula (I) or a pharmaceutically acceptable salt thereof as claimed in any one of claims 1–8.

* * * * *